Figure 1:
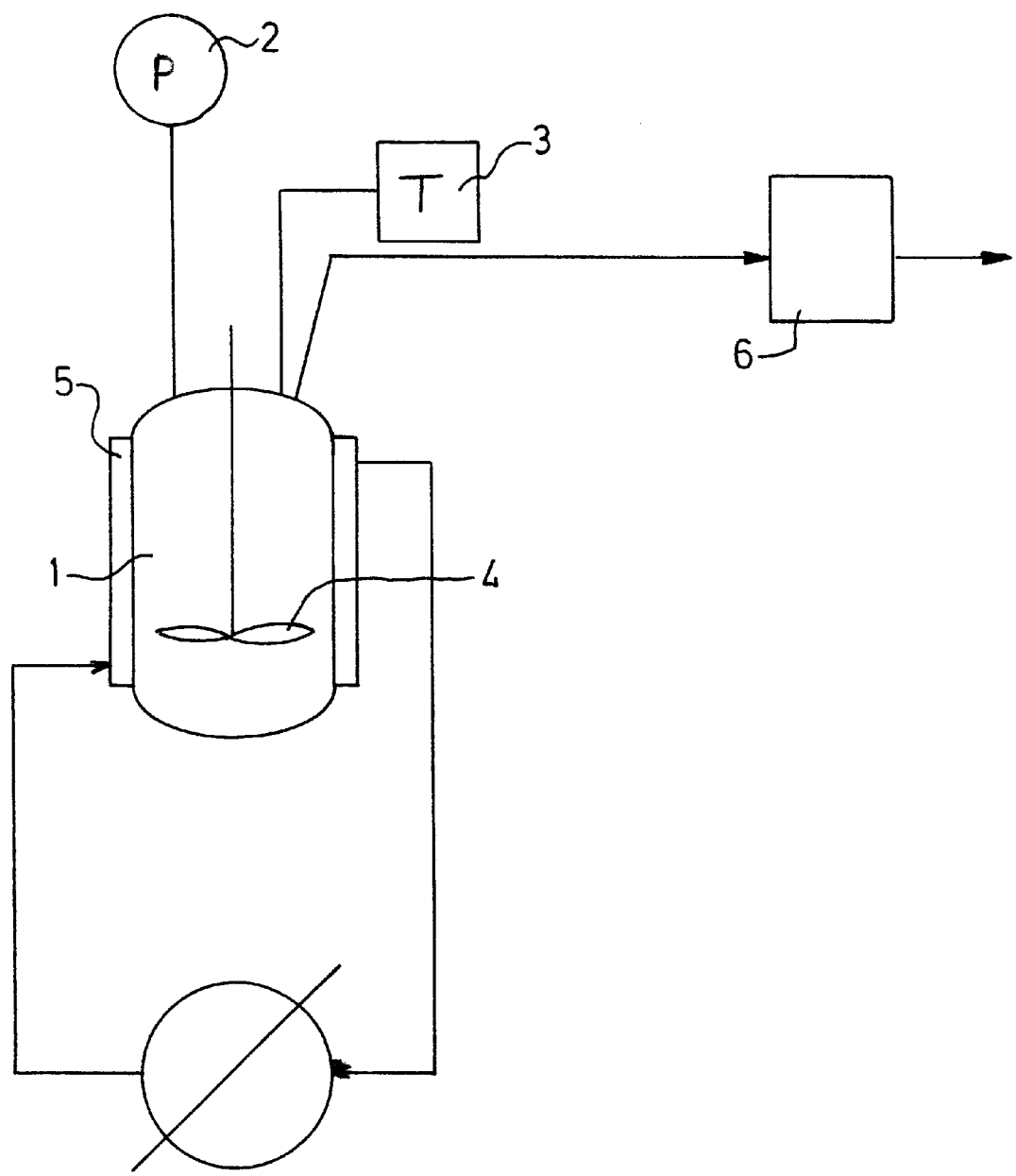

United States Patent [19]
Claude et al.

[11] Patent Number: 6,025,504
[45] Date of Patent: Feb. 15, 2000

[54] METHOD FOR PREPARING GLYCEROL CARBONATE

[75] Inventors: Sylvain Claude, Paris; Zéphirin Mouloungui, Toulouse; Jeong-Woo Yoo, Toulouse; Antoine Gaset, Toulouse, all of France

[73] Assignee: Organisation Nationale Interprofessionnelle des Oleagineux (O.N.I.D.OL.), Paris, France

[21] Appl. No.: 09/296,173

[22] Filed: Apr. 22, 1999

[30]     Foreign Application Priority Data

Apr. 30, 1998 [FR] France ................................. 98.05547

[51] Int. Cl.⁷ .................................................. C07D 317/36
[52] U.S. Cl. .............................................................. 549/229
[58] Field of Search ................................................ 549/229

[56]              References Cited
              U.S. PATENT DOCUMENTS 2,915,529  12/1959  Bell et al. ............................... 549/229

FOREIGN PATENT DOCUMENTS 0 443 758 A1   8/1991   European Pat. Off. .
0 581 431 A2   2/1994   European Pat. Off. .
2 733 232     10/1996   France .

OTHER PUBLICATIONS

Abbas–Alli G. Shaikh et al., "Organic Carbonates", Chemical Reviews, 1996 vol. 96, No. 3, pp. 951–976, *American Chemical Society*.

Peter Ball et al., "Synthesis of Carbonates and Polycarbonates by Reaction of Urea with Hydroxy Compounds", 1984, vol. 1, pp. 95–108, *Harwood Academic Publishers GMBH*.

*Primary Examiner*—Bernard Dentz
*Attorney, Agent, or Firm*—Young & Thompson

[57]              ABSTRACT

The invention concerns a method for preparing glycerol carbonate. This method consists of making urea and glycerol react at a temperature substantially between 90° C. and 220° C. in the presence of a catalyst bearing Lewis acid sites, in particular metallic or organometallic salts or supported metallic compounds. The invention enables glycerol carbonate to be obtained, by a catalytic carbamoylation/carbonation reaction, in a highly pure state under economic conditions.

13 Claims, 1 Drawing Sheet

METHOD FOR PREPARING GLYCEROL CARBONATE

The invention concerns a method for preparing glycerol carbonate:

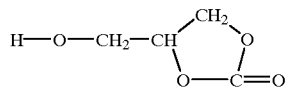

Glycerol carbonate is a bifunctional compound and its dual functionality enables it to act as a solvent for many organic or inorganic compounds (in the field of cosmetics, paints, accumulators etc). This protic polar solvent is sought after by reason of its non-toxicity and high boiling point. Glycerol carbonate may also act as an additive for stabilizing polymers, polymerization monomers for the synthesis of polycarbonates, and synthetic intermediates in certain organic reactions (esterification, transesterification, carbamoylation etc).

However, this compound is not at present manufactured on the industrial scale. It is obtained in the laboratory by the reaction of glycerol with an organic carbonate (patents U.S. Pat. No. 2,915,529, FR 2 733 232). The essential shortcoming in this glycerol carbonation reaction lies in the cost of the reagent used as the source of carbonate.

The object of the invention is to provide a novel method for preparing glycerol carbonate by a catalytic carbamoylation/carbonation reaction of glycerol using a much less expensive reagent than organic carbonates.

Another object is to obtain glycerol carbonate in a state of high purity without the necessity of separating byproducts.

Another object is to enable glycerol carbonate to be obtained from impure starting reagents, in particular commercially available impure compounds.

To this end, the method according to the invention for the preparation of glycerol carbonate consists of making urea react with glycerol at a temperature substantially between 90° C. and 220° C. in the presence of a catalyst bearing Lewis acid sites associated with one or more hetero-atomic (namely not carbon-based) anionic counterions.

The catalyst may in particular consist of a metallic or organometallic salt, or a mixture of metallic or organometallic salts, in the form of a powdered solid. A supported metallic compound can also be used in a macroporous solid form or as a gel, comprising an organic polymeric matrix supporting, on hetero-organic functional groups, metal cations provided with Lewis acid sites.

Accordingly, the method of the invention uses urea as the starting reagent, which is a cheap compound available in large quantities. Experiments have shown that this reagent reacts with glycerol when heated in the presence of a catalyst of the previously mentioned type according to the following mechanism:

(1) urea+glycerol→glycerol carbamate+ammonia (2) glycerol carbamate→glycerol carbonate+ammonia.

The second step has slower kinetics than the first but the presence of the catalyst prevents this step being a blocking one. The reaction is preferably carried out under vacuum, in particular at a pressure of between $10^3$ and $2.10^4$ pascals, so as to displace the point of equilibrium of the reactions by eliminating ammonia in the gaseous state.

Experiments have shown that glycerol could be added in the form of so-called technical glycerine, resulting from basic lipochemical reactions (alcoholysis, hydrolysis, saponification of animal or vegetable oils or fats).

It has been shown that metallic sulfates or organometallic sulfates (or a mixture of sulfates) give a very good catalytic efficiency, the metallic cation being preferably chosen so that the salt has a cold water solubility greater than 5 g per liter. It has also been shown that preliminary calcination of this type of catalyst is advantageous in order to increase its catalytic activity (this calcination reduces the number of Brönsted sites). In particular, a metallic sulfate can be used (or a mixture of sulfates) of the following group: manganese sulfate, zinc sulfate, magnesium sulfate, nickel sulfate, iron sulfate and cobalt sulfate. A zinc organometallic sulfate can also be used. These solid sulfates have many Lewis acid sites which have a high activity (particularly following calcination), sites which are responsible for most of the catalytic activity, bringing about very efficient activation of the carbonation step (2). The metallic catalyst of the type referred to above is preferably added in a weight proportion (based on glycerol) substantially between 1% and 8%, the value chosen within this range depending on the number and strength of the Lewis acid sites which the salt used contains.

As already mentioned, a supported metallic compound may also be used as a catalyst comprising a polymeric matrix, in particular a polystyrene matrix, supporting metallic cations, in particular $Zn^{++}$, $Mg^{++}$, $Mn^{++}$, $Fe^{++}$, $Ni^{++}$, $Cd^{++}$; associated with hetero-organic functional groups, in particular sulfonates. Such a supported metallic compound may advantageously be produced by ion exchange from a commercially available sulfonic polymeric matrix. Exchange is carried out so as to attach metal cations provided with Lewis acid sites to the sulfonate groups of the said matrix. The addition of the supported metallic compound of the aforementioned type is preferably carried out so that the quantity of metal cations per mole of glycerol is substantially between 10 and 100 milli-equivalent gram.

In the case where such a supported metallic compound is used, it is desirable that the reaction medium is anhydrous so as to eliminate any risk of degradation of the catalyst. According to a preferred embodiment, glycerol and the catalyst are first of all put under the aforementioned reduced pressure with evacuation of the water vapor evolved, urea being then added after the free water is eliminated from the reaction mixture.

In addition, the quantities of urea and glycerol mixed are advantageously adjusted so that the relative molar proportions of these compounds lies between 0.65 and 1.20 mole of urea per mole of glycerol. Optimum coupling is thus obtained between the two steps:carbamoylation (1) and carbonation (2).

The carbamolylation (1) and carbonation (2) reactions used in the process of the invention have never been used with glycerol for obtaining glycerol carbonate. It should be noted that the carbonation reactions involving urea have already been described starting either with a mono-alcohol ("Shaikh and Sivaram, Organic Carbonates, Chem. Rev. 1996, 96, p 951–976"; "Ball et al, Synthesis of carbonates and polycarbonates by reaction of urea with hydroxy compounds, Mol. Chem. 1984, vol. 1, p 95–108") or starting from a diol (EP 0 443 758; EP 0 581 131). However, the recommended catalysts for these reactions carried out with a mono-alcohol or a diol are mostly ineffective in the case of glycerol (and more particularly in the case of triols) as shown in the comparative tests E–H provided hereinafter.

The following examples 1 to 21 and the comparative tests A to H were used in an installation operating discontinuously such as shown in FIG. 1.

This installation comprised a semi-closed reactor 1 (250 ml) provided with a pressure sensor 2, a temperature sensor 3, a mechanical stirrer 4, a jacket 5 containing a heating oil bath, and a vacuum pump 6 for extracting vapors and ammonia, enabling the pressure to be adjusted to a value of approximately 40 mbar (approximately $4.10^3$ pascals).

Unless stated to the contrary, the yields provided in the examples and comparative tests are molar yields of glycerol carbonate based on the starting glycerol.

EXAMPLE 1

27.6 g (0.3 mole) of glycerol, 18.0 g (0.3 mole) of urea and 1.7 g of manganese sulfate calcined at 450° C. for 3 hours, (urea/glycerol molar ratio=1; weight proportion catalyst/glycerol=0.086) were mixed in the reactor 1 of FIG. 1. The reaction mixture was brought to 150° C. and the pressure was reduced to 40 mbar with mechanical stirring for 2 hours. The ammonia formed during the reaction was eliminated by the vacuum pump 6. After 2 hours, the impure reaction mixture was analyzed by gas chromatography on a "Carbowax 20 M" capillary column (12 m) with tetraethylene glycol as the internal standard. 16.8 g (0.183 mole) of glycerol were converted into 21.6 g of glycerol carbonate (i.e. a molar yield of 61% based on glycerol).

EXAMPLE 2

The method used was identical to that of example 1, but the quantity of catalyst was reduced and the reaction time increased. 0.5 g of manganese sulfate were used, calcined at 450° C. (weight ratio catalyst/glycerol=0.027). The reaction was carried out at 150° C. and 40 mbar for 6 hours. After 6 hours the impure reaction mixture was analyzed by gas chromatography on a "Carbowax 20 M" capillary column (12 m) with tetraethylene glycol as the internal standard. 20.2 g (0.22 mole) of glycerol were converted into 26.0 g of glycerol carbonate (i.e. a molar yield of 73% based on glycerol).

EXAMPLES 3–4

27.6 g (0.3 mole) of glycerol, 18.0 g (0.3 mole) of urea and 1.7 g of magnesium sulfate, calcined at 375° C. for 3 hours, were mixed in the reactor 1 of FIG. 1. The reaction mixture was brought to 150° C., and the pressure was reduced to 40 mbar with mechanical stirring for 2 hours (example 3) and for 5 hours (example 4). The ammonia formed during the reaction was eliminated by the vacuum pump 6. After the reaction, the impure reaction mixture was analyzed by gas chromatography on a "Carbowax 20 M" capillary column (12 m) with tetraethylene glycol as the internal standard. The molar yields based on glycerol are indicated in the following table:

| Example | Reaction time (h) | Yield (%) |
| --- | --- | --- |
| 3 | 2 | 44 |
| 4 | 5 | 58 |

EXAMPLE 5

The method used in this example was identical to that of example 4, but the urea/glycerol/molar ratio was changed. 27.6 g (0.3 mole) of glycerol, 12.0 g (0.2 mole) of urea and 1.7 g of magnesium sulfate, calcined at 375° C. for 3 hours, (urea/glycerol molar ratio=0.67) were mixed together. The reaction was carried out at 150° C. and 40 mbar for 5 hours. After 5 hours the impure reaction mixture was analyzed by gas chromatography on a "Carbowax 20 M" capillary column (12 m) with tetraethylene glycol as the internal standard. 14.7 g (0.16 mole) of glycerol were converted into 18.9 g of glycerol carbonate (i.e. a molar yield of 81% based on urea and a molar yield of 54% based on glycerol).

EXAMPLES 6–7

27.6 g (0.3 mole) of glycerol, 18.0 g (0.3 mole) of urea and 1.5 g of cobalt sulfate, calcined at 450° C. for 3 hours, (weight ratio catalyst/glycerol=0.077) were mixed in the reactor 1 of FIG. 1. The reaction mixture was brought to 150° C. and the pressure was reduced to 40 mbar with mechanical stirring for 2 hours (example 6) and for 5 hours (example 7). The ammonia formed during the reaction was eliminated by the vacuum pump 6. After the reaction, the impure reaction mixture was analyzed by gas chromatography on a "Carbowax 20 M" capillary column (12 m) with tetraethylene glycol as the internal standard. The molar yields based on glycerol are indicated in the following table:

| Example | Reaction time (h) | Yield (%) |
| --- | --- | --- |
| 6 | 2 | 51 |
| 7 | 5 | 63 |

EXAMPLES 8–10

The method used in these examples was identical to that of example 1, while using other catalysts. The catalysts used and the molar yields based on glycerol, after 2 hours reaction, are indicated in the following table:

| Example | Catalyst | Yield | Comments |
| --- | --- | --- | --- |
| 8 | $FeSO_4$ | 41 | Calcined at 400° C. |
| 9 | $FeSO_4 \cdot 7H_2O$ | 37 | Not calcined |
| 10 | $ZnSO_4$ | 80 | Calcined at 550° C. |

EXAMPLE 11

27.6 g (0.3 mole) of glycerol, 18.0 g of urea and 1.7 g of zinc sulfate were mixed in the reactor 1 of FIG. 1. The reaction mixture was brought to 130° C. and the pressure was reduced to 40 mbar with mechanical stirring for 5 hours. The ammonia formed during the reaction was eliminated by the vacuum pump 6. After 5 hours the impure reaction mixture was analyzed by gas chromatography on a "Carbowax 20 M" capillary column (12 m) with tetraethylene glycol as the internal standard. 22.9 g (0.25 mole) of glycerol were converted into 29.4 g of glycerol carbonate (i.e. a molar yield of 83% based on glycerol).

Comparative reference test A (absence of catalyst)

The method used in example 1 was reproduced but in the absence of a catalyst so as to compare the yields of glycerol carbonate obtained.

A molar yield of 26% was obtained based on glycerol.

Comparative tests B, C, D

The method used for these comparative tests was identical to that of example 1 while using insoluble catalysts (cold water solubility less than 5 g/l) having few Lewis acid sites. A comparison of these tests with the preceding examples showed the effectiveness of the Lewis sites in the catalyst. It should be noted that, for test D, strontium sulfate was calcined but that this treatment did not increase the carbonate yield significantly. In test B, it seems that the insoluble strontium sulfate had a rather unfavorable effect (compared with the reference test A), probably by reason of the number of Brönsted sites. The catalysts used and the molar yield, based on glycerol, after 2 hours reaction, are indicated in the following table:

| Test Number | Catalyst | Yield | Comments |
|---|---|---|---|
| B | $SrSO_4$ | 25 | Not calcined |
| C | $BaSO_4$ | 28 | Not calcined |
| D | $SrSO_4$ | 27 | Calcined at 400° C. |

Comparative tests E–H

The method used in example 1 and the reference test A were reproduced using certain catalysts recommended in the prior art for carbonation reactions involving urea. The catalysts used and the molar yield based on glycerol are indicated in the following table:

| Test | Catalyst | Yield | Comment: Catalyst recommended in: |
|---|---|---|---|
| E | Dibutyltin oxide (1 g) | 27 | EP 0 443 758 |
| F | Magnesium oxide (1 g) | 32 | EP 0 581 131 |
| G | Lead acetate (1 g) | 28 | EP 0 581 131 |
| H | Calcium chloride (1 g) | 25 | EP 0 581 131 |

The effectiveness of these catalysts on the reaction of urea with glycerol was very low, or even zero.

EXAMPLE 12

27.6 g (0.3 mole) of glycerol, 18.0 g (0.3 mole) of urea and 1.7 g of zinc p-toluene sulfate hydrate were mixed in the reactor 1 of FIG. 1. The reaction mixture was brought to 145° C. and the pressure was reduced to 50 mbar with mechanical stirring for 1.25 hours. The ammonia formed during the reaction was eliminated by the vacuum pump 6. After 1.25 hours the impure reaction mixture was analyzed by gas chromatography on a "Carbowax 20 M" capillary column (12 m) with tetraethylene glycol as the internal standard. 23.4 g (0.26 mole) of glycerol were converted into 30.1 g (mole) of glycerol carbonate (i.e. a molar yield of 85% based on glycerol).

EXAMPLE 13

A strong acid resin gel in the $Na^+$ form (trade name "Bayer Lewatit VP OC 1800"), pre-swollen in water, was exchanged into the $Zn^{++}$ form by percolating a 2N $ZnSO_4$ solution (5 volumes for 1 volume of resin). The exchanged resin was rinsed with demineralized water until free $ZnSO_4$ had been eliminated (10 volumes for 1 volume of resin). It was washed with ethanol and then with diethyl ether. It was then dried under vacuum using a filter pump and stored in a desiccator. It contained 1 meq.g of $Zn^{++}$ per ml.

27.6 g (0.3 mole) of glycerol and 8 g (i.e. substantially 8 ml) of the resin as prepared above were mixed in the reactor 1 of FIG. 1. The reaction mixture was brought to 130° C. and the pressure was reduced to 40 mbar with mechanical stirring for 5 minutes to eliminate water until water vapor was no longer evolved. Almost all the water in the resin was eliminated in this way. 18.0 g (0.3 mole) or urea were then added and the reaction was carried out for 5 hours at 130° C. and 40 mbar with mechanical stirring. The ammonia formed during the reaction was eliminated by the vacuum pump 6. After 5 hours, the impure reaction mixture was analyzed by gas chromatography on a "Carbowax 20 M" capillary column (12 m) with tetraethylene glycol as the internal standard. 22.0 g (0.24 mole) of glycerol were converted into 28.2 g of glycerol carbonate (i.e. a molar yield of 80% based on glycerol).

EXAMPLE 14

A strong acid macroporous resin in the $H^+$ form (trade name "Bayer K2431"), pre-swollen in water, was exchanged into the $Na^+$ form by percolating a 2N NaOH solution (5 volumes for 1 volume of resin). The exchanged resin was rinsed with demineralized water until an effluent was obtained with a neutral pH. It was then exchanged into the bivalent metal form $M^{++}$ by percolating an $MSO_4$ solution corresponding to 1N (5 volumes for 1 volume of resin). The metal differed according to the examples: $Zn^{++}$: ex. 14; $Mn^{++}$: ex. 15; $Mg^{++}$: ex. 16; $Fe^{++}$: ex. 17; $Ni^{++}$: ex. 18; $Cd^{++}$: ex. 19. The exchanged resin was rinsed with demineralized water until the free $MSO_4$ was eliminated (10 volumes for 1 volume of resin). It was washed with ethanol and then diethyl ether. It was then dried under vacuum using a filter pump and stored in a desiccator. It contained 0.5 meq.g of $M^{++}$ per ml.

The method used for example 14 was identical to that of example 13 but the catalyst was changed for the resin in the $Zn^{++}$ form described above (quantity: 8 g, i.e. 8 ml). After 5 hours, 22.1 g (0.24 mole) of glycerol were converted into 28.4 g of glycerol carbonate (i.e. a molar yield of 81% based on glycerol).

EXAMPLES 15–19

The method used was identical to that of the preceding example, but the reaction temperature was changed, it being adjusted to 145° C., and the catalyst was chosen from among the resins whose preparation is described in the preceding example in the $Mn^{++}$, $Mg^{++}$, $Fe^{++}$, $Ni^{++}$, $Cd^{++}$ form. After 2 hours reaction, the impure reaction mixture was analyzed by gas chromatography on a "Carbowax 20 M" capillary column (12 m) with tetraethylene glycol as the internal standard. The yields are indicated in the following table.

| Example number | Catalyst | Yield in 2 h (%) |
|---|---|---|
| 15 | $P-SO_3Mn$ | 63 |
| 16 | $P-SO_3Mg$ | 58 |
| 17 | $P-SO_3Fe$ | 61 |
| 18 | $P-SO_3Ni$ | 60 |
| 19 | $P-SO_3Cd$ | 57 |

EXAMPLE 20

42.5 g of technical glycerol (namely a commercially available product containing 65% glycerol), i.e. 0.3 mole of glycerol, were poured into the reactor 1 of FIG. 1. The reaction mixture was brought to 130° C. and the pressure was reduced to 40 mbar with mechanical stirring for 15 minutes to eliminate water. Virtually all the water provided by the glycerol was eliminated in this way. 18.0 g (0.3 mole)

of urea and 1.7 g of zinc sulfate (33 meq.g/mole of glycerol) were then added. The reaction was carried out for 5 hours at 130° C. and 40 mbar with mechanical stirring. The ammonia formed during the reaction was eliminated by the vacuum pump 6. After 5 hours the impure reaction mixture was analyzed by gas chromatography on a "Carbowax 20 M" capillary column (12 m) with tetraethylene glycol as the internal standard. 21.8 g (0.237 mole) of glycerol were converted into 28.0 g of glycerol carbonate (i.e. a molar yield of 79% based on glycerol). It was thus found that the method of the invention gave a good result when using an ordinary type of impure glycerol (so-called technical glycerol) as the starting material.

EXAMPLE 21

42.5 g of technical glycerol (65% glycerol), i.e. 0.3 mole of glycerol, were poured into the reactor 1 of FIG. 1. The reaction mixture was brought to 130° C. and the pressure was reduced to 40 mbar with mechanical stirring for 15 minutes to eliminate water. 8 g of the resin prepared in example 13 in the $Zn^{++}$ form were then added and the reaction mixture was brought to 130° C. and the pressure was reduced to 40 mbar with mechanical stirring for 5 minutes to eliminate the water in the resin. After introducing 18.0 g (0.3 mole) of urea, the reaction was carried out for 5 hours at 130° C. and 40 mbar with mechanical stirring. The ammonia formed during the reaction was eliminated by the vacuum pump 6. After 5 hours reaction, 20.7 g (0.225 mole) of glycerol were converted into 26.6 g of glycerol carbonate (i.e. a molar yield of 75% based on glycerol).

We claim:

1. A method for preparing glycerol carbonate, wherein urea and glycerol are made to react at a temperature substantially between 90° C. and 220° C. in the presence of a catalyst bearing Lewis acid sites associated with one or more hetero-atomic anionic counterions.

2. The method for preparing glycerol carbonate as claimed in claim 1, wherein a metallic or organometallic sulfate is used as a catalyst, in the form of a powdered solid, the metal cation of the said sulfate being chosen so that the salt has a cold water solubility greater than 5 g per liter.

3. The method for preparing glycerol carbonate as claimed in claim 1, wherein a metallic or organometallic sulfate is used which has been previously subjected to calcination.

4. The method for preparing glycerol carbonate as claimed in claim 2, wherein use is made of a metallic or organometallic sulfate or a mixture of metallic or organometallic sulfates from the following group: manganese sulfate, zinc sulfate, magnesium sulfate, nickel sulfate, iron sulfate, cobalt sulfate or an organometallic sulfate of zinc.

5. The method for preparing glycerol carbonate as claimed in claim 2, wherein the metallic or organometallic sulfate is added in a weight proportion based on glycerol substantially between 1% and 8%.

6. The method for preparing glycerol carbonate as claimed in claim 1, wherein a supported metallic compound is used as a catalyst in the form of a macroporous solid or of a gel, said compound comprising an organic polymeric matrix supporting, on hetero-organic functional groups, metal cations provided with Lewis acid sites.

7. The preparative method as claimed in claim 6, wherein a supported metallic compound is used, obtained from a sulfonic polymeric matrix by ion exchange, able to attach metal cations provided with Lewis acid sites onto its functional groups.

8. The preparative method as claimed in claim 6, wherein a supported metallic compound is used comprising, on the one hand, a polystyrene polymeric matrix and, on the other hand, one or more cations of the following group: $Zn^{++}$, $Mg^{++}$, $Mn^{++}$, $Fe^{++}$, $Ni^{++}$, $Cd^{++}$, associated with the sulfonate groups of the polystyrene matrix.

9. The preparative method as claimed in claim 6, wherein the supported metallic compound is added so that the quantity of metal cations per mole of glycerol is substantially between 10 and 100 milli-equivalent gram.

10. The preparative method as claimed in claim 1, wherein the pressure of the reaction medium is adjusted within a range substantially between $10^3$ and $2.10^4$ pascals.

11. The preparative method as claimed in claim 10, wherein glycerol and the catalyst are first of all mixed at the aforementioned reduced pressure with evacuation of the water vapor evolved, urea being then added after free water has been eliminated from the reaction medium.

12. The preparative method as claimed in claim 1, wherein the quantities of urea and glycerol mixed are adjusted so that the relative molar proportions of these compounds lie between 0.65 and 1.20 mole of urea per mole of glycerol.

13. The preparative method as claimed in claim 1, wherein glycerol is added in the form of technical glycerine.

* * * * *